United States Patent [19]

Hasegawa

[11] Patent Number: 5,221,943
[45] Date of Patent: Jun. 22, 1993

[54] IMAGE FORMING APPARATUS

[75] Inventor: Hirofumi Hasegawa, Osaka, Japan

[73] Assignee: Minolta Camera Kabushiki Kaisha, Osaka, Japan

[21] Appl. No.: 900,793

[22] Filed: Jun. 22, 1992

Related U.S. Application Data

[63] Continuation of Ser. No. 737,807, Jul. 29, 1991, abandoned, which is a continuation of Ser. No. 477,751, Feb. 9, 1990, abandoned.

[30] Foreign Application Priority Data

Feb. 10, 1989 [JP] Japan ................................. 1-31821

[51] Int. Cl.$^5$ ........................................... G03G 15/06
[52] U.S. Cl. .................................... 355/245; 346/160; 355/200; 355/210; 358/296
[58] Field of Search ............... 355/200, 210, 211, 202, 355/213, 245; 346/160; 358/300, 296

[56] References Cited

U.S. PATENT DOCUMENTS

| | | | |
|---|---|---|---|
| 4,128,079 | 12/1978 | Suzuki | 118/658 |
| 4,571,060 | 2/1986 | Bares | 355/200 |
| 4,575,221 | 3/1986 | Onoda et al. | 355/200 |
| 4,588,280 | 5/1986 | Ogawa et al. | 355/200 |
| 4,634,264 | 1/1987 | Takahashi | 355/200 |
| 4,785,319 | 11/1988 | Fujino et al. | 346/160 |
| 4,791,454 | 12/1988 | Takahashi et al. | 355/299 |
| 4,876,572 | 10/1989 | Nagatsuna | 355/200 X |
| 4,926,219 | 5/1990 | Hirasawa et al. | 355/200 X |

FOREIGN PATENT DOCUMENTS

0116976 2/1984 European Pat. Off. .
0068859 3/1988 Japan ................................. 355/200

Primary Examiner—A. T. Grimley
Assistant Examiner—Sandra L. Brase
Attorney, Agent, or Firm—Burns, Doane, Swecker & Mathis

[57] ABSTRACT

An image-forming apparatus includes an image-forming unit detachably attached to a body of the apparatus, a holding member attached to the unit, and an engaging member attached to the body. The unit has a photosensitive member rotatably in a first rotary axis, and a roller member rotatably in a second rotary axis. The holding member has a first holding portion for holding the first rotary axis, a second holding portion for holding the second rotary axis, and a positioning member, whereby the photosensitive member and the roller member is held at specific intervals in the image-forming unit. The engaging member brings into engagement with the positioning member when the image-forming unit is attached to the body, whereby the image-forming unit is positioned to the body. A method, in the apparatus, includes the steps of attaching the holding member to the unit; holding the photosensitive member and the roller in the unit at specific intervals by the holding member; attaching the positioning member to the body; and contacting the positioning member with the holding member when the unit is attached to the body, whereby the unit is positioned to the body.

31 Claims, 10 Drawing Sheets

IMAGE FORMING APPARATUS

This application is a continuation of application Ser. No. 07/737,807, filed Jul. 29, 1991, now abandoned which is a continuation of application Ser. No. 07/477,751, filed Feb. 9, 1990 now abandoned.

BACKGROUND OF THE INVENTION

The present invention relates to an image-forming apparatus such as a copy apparatus or a printer.

Generally, in such an image-forming apparatus that developer on a roller or a developer-holding member attached to the outer surface of the roller is brought into contact with a photosensitive drum to develop an electrostatic latent image on the drum to form a visible image, maintaining a distance between the drum and the roller constant along the axes thereof is necessary in order to form an image of uniform density.

In another image-forming apparatus in which an image-forming unit unitedly assembled by a photosensitive drum and a developing device is attached to a body of the apparatus, it is necessary for the unit to be accurately located with respect to the body and to connect the drum with a driving system of the body with good accuracy.

Therefore, conventionally, a distance between the drum and the roller is set to be constant by bringing contact members arranged at both the ends of the roller into contact with the drum. A positioning member of the unit is engaged with an engaging portion of the body, so that the unit is positioned to the body of the apparatus.

Deformation such as errors or torsion in manufacturing the body of the unit, however, causes the drum not to be positioned to the body of the apparatus with good accuracy, and thus looseness causes in engagement between a driving gear of the drum and a gear of the driving system of the body.

SUMMARY OF THE INVENTION

Accordingly, an essential object of the present invention is to provide an image-forming apparatus capable of resolving the disadvantage.

In accomplishing these and other objects, according to one preferred embodiment of the present invention, there is provided an image-forming apparatus comprising: an image-forming unit detachably attached to a body of the apparatus and having a photosensitive member rotatably in a first rotary axis, and a roller member rotatably in a second rotary axis; a holding member attached to said image-forming unit and having a first holding portion for holding the first rotary axis, a second holding portion for holding the second rotary axis, and a positioning member, whereby the photosensitive member and the roller member being held at specific intervals in said image-forming unit; and an engaging member attached to the body thereof and bringing into engagement with the positioning member when said image-forming unit is attached to the body, whereby said image-forming unit is positioned to the body.

In another aspect of the present invention, the image-forming apparatus has an image-forming unit detachably attached to a body of the apparatus, the image-forming unit integrally holding, at least, a photosensitive member and a developing roller, the apparatus comprising: a first frame having a holding means for detachably holding the image-forming unit, and an exposure means for forming an electrostatic latent image on an outer surface of the photosensitive member in the image-forming unit by exposure; a second frame holding said first frame to be capable of opening and closing it with respect thereto, and having a copy paper transporting means, a transfer means for transferring the image on the photosensitive member onto the paper, and a driving force transferring means for transferring a driving force to the image-forming unit; a holding member attached to the image-forming unit, having a first holding portion for holding a rotary shaft of the photosensitive member, a second holding portion for holding a rotary shaft of the developing roller, and a positioning member, whereby said holding member holding the photosensitive member and the developing roller which are spaced at specific intervals in the image-forming unit; and an engaging member attached to said second frame, and bringing into engagement with the positioning member when said first frame holding the image-forming unit is closed with respect to said second frame, whereby the image-forming unit is positioned at a specified position with respect to said second frame.

In a further aspect of the present invention, there is provided a method, in an image-forming apparatus having an image-forming unit detachable attached to a body of the apparatus, the image-forming unit integrally holding, at least, a photosensitive member and a developing roller, comprising the steps of: attaching a holding member to the image-forming unit; holding the photosensitive member and the developing roller in the image-forming unit at specific intervals by the holding member; attaching a positioning member to the body; and contacting the positioning member with the holding member when the image-forming unit is attached to the body, whereby the image-forming unit is positioned to the body.

By the above construction of the present invention, the photosensitive member and the roller member are held spacing at specific intervals by the holding member and the holding member is positioned to the body with the engagement between the holding member and the engaging member. Therefore, both the members can be accurately positioned to the body in a specific position. Then, developer can be uniformly supplied onto the latent image on the photosensitive member to get a uniform image. When the photosensitive member has the second driving force transferring unit, the unit can be brought into engagement with the first driving force transferring unit of the body with high accuracy to smoothly transfer the driving force from the first driving force transferring unit to the photosensitive member without looseness.

BRIEF DESCRIPTION OF THE DRAWINGS

These and other objects and features of the present invention will become clear from the following description taken in conjunction with the preferred embodiments thereof with reference to the accompanying drawings, in which.

DETAILED DESCRIPTION OF THE EMBODIMENTS

Before the description of the present invention proceeds, it is to be noted that like parts are designated by like reference numerals throughout the accompanying drawings.

Figure 1:
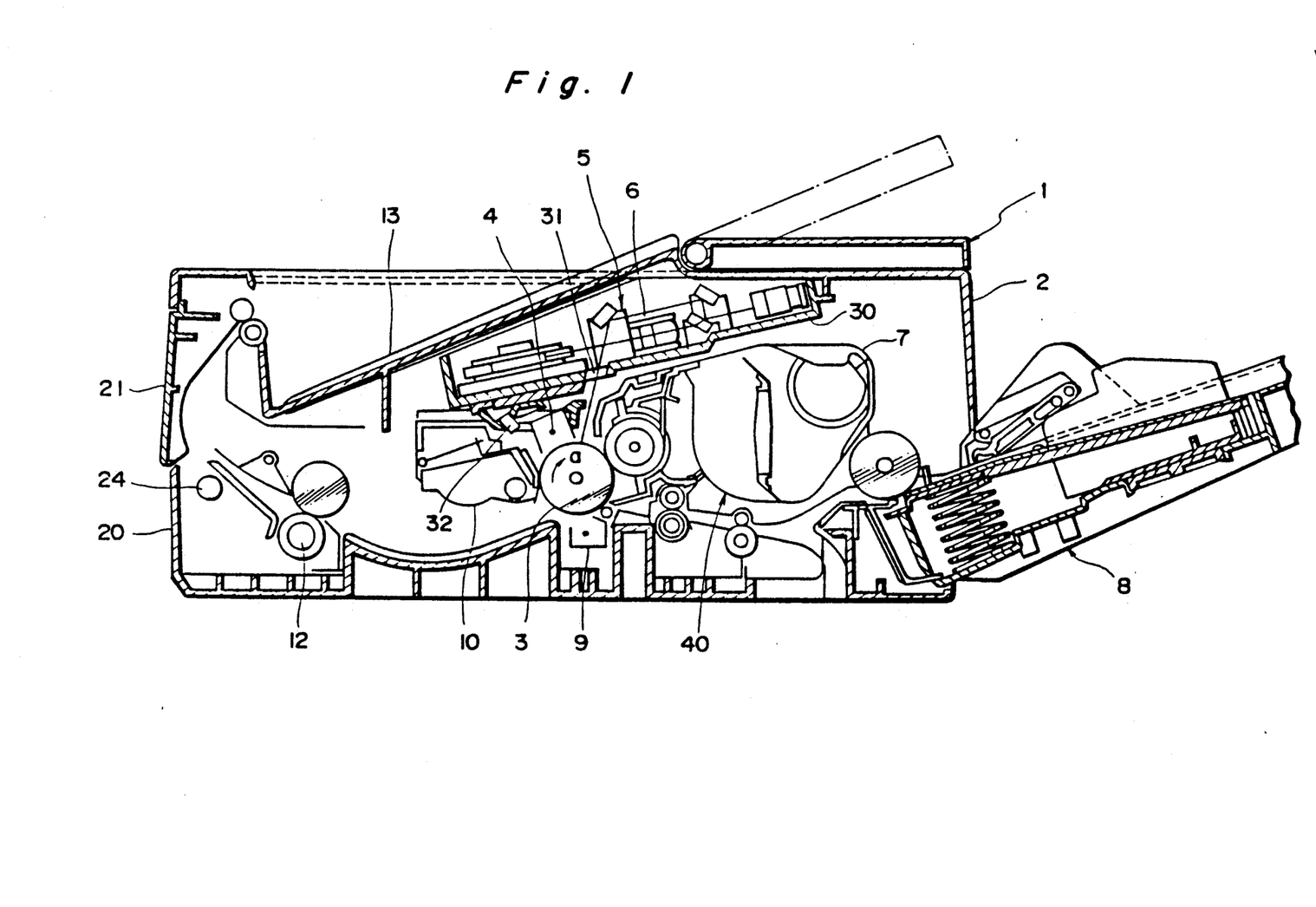
FIG. 1 is a sectional view of a printer of a preferred embodiment according to the present invention.

FIG. 1 shows a printer 1 which construction will be described hereinbelow.

Figure 2:
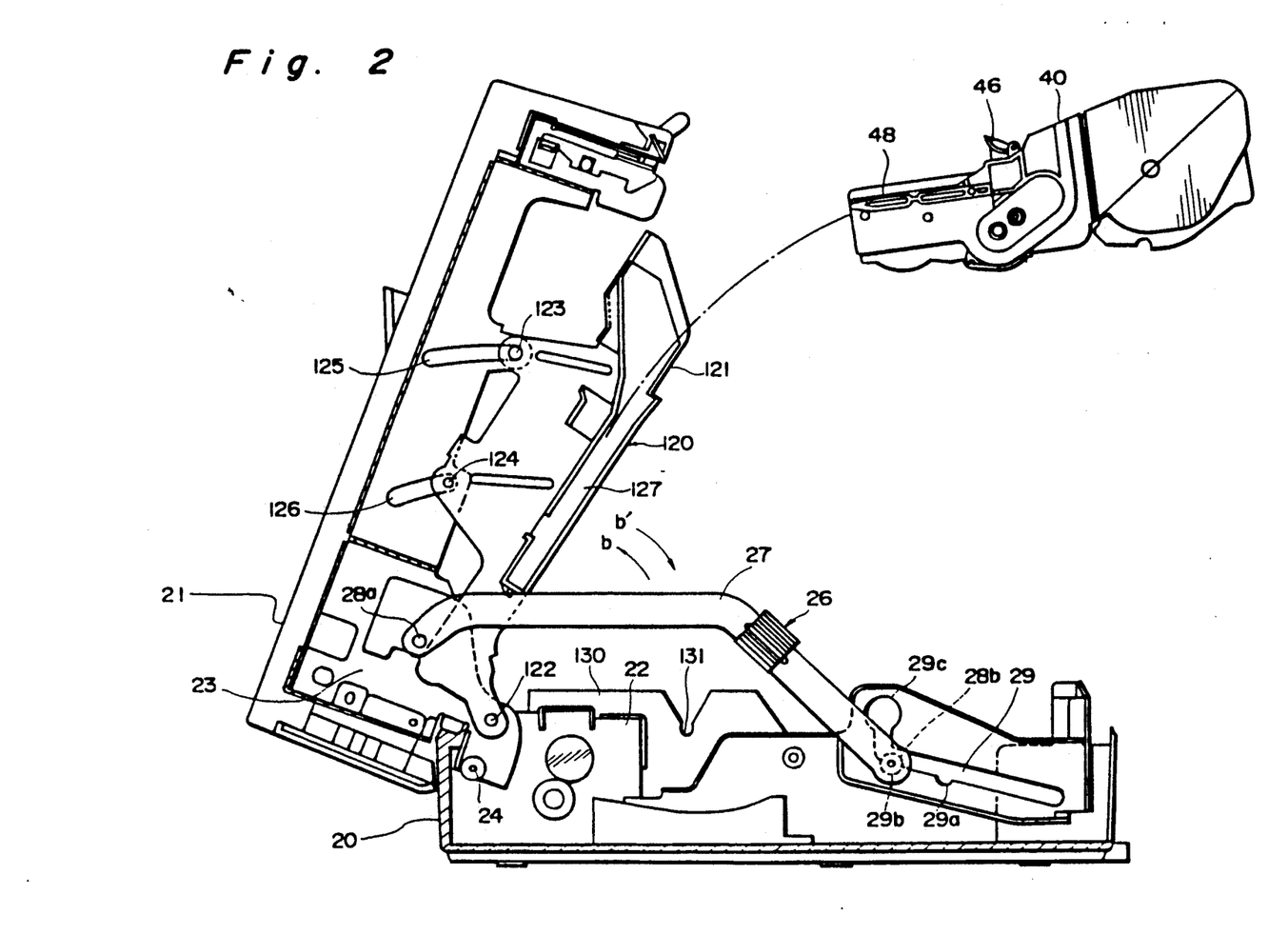
FIG. 2 is a sectional view of the printer in a state where an upper unit thereof is opened with respect to a lower unit thereof.

A BODY 2 (REFERRING TO FIGS. 1 AND 2)

A body 2 of the printer 1 is divided into two parts, a lower unit 20 and an upper unit 21. The unit 20 has a side frame 22 at both the sides thereof and the unit 21 has a side frame 23 at both the sides thereof The side frames 22 and 23 are rotatably connected with each other through a shaft 24 to rotate the upper unit 21 with respect to the lower unit 20 in directions shown by arrows (b) and (b,) for opening and closing.

The upper unit 21 is urged in the direction shown by the arrow (b) for opening thereof by a spring (not shown) and is held in an open state by an open holding mechanism 26.

In the mechanism 26, an arm 27 is rotatably attached to the side frame 23 of the upper unit 21 with a pin 28a. A pin 28b arranged at the free end of the arm 27 is inserted into a guide groove 29 arranged at the side frame 22 of the lower unit 21. The groove 29 has engaging portions 29a, 29b, and 29c. According to the opening and closing operations of the upper unit 21, the pin 28b is moved in the groove 29. By engaging the pin 28b with one of the engaging portions 29a, 29b, and 29c, the upper unit 21 is held in the opening state at a specified angle predetermined with respect to the engaging portion with which the pin 28b is engaged.

B. OPTICAL UNIT 5 (REFERRING TO FIGS. 1 AND 3)

Figure 3:
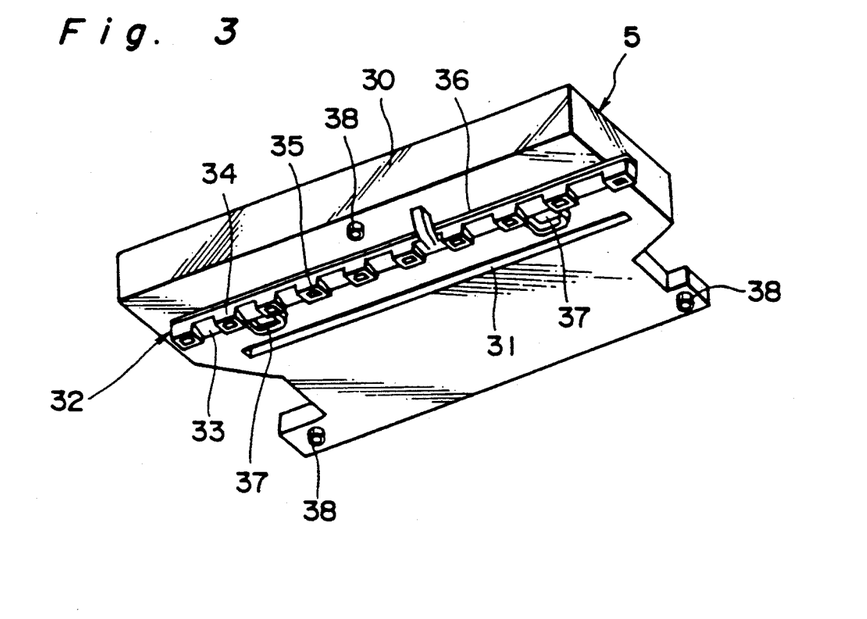
FIG. 3 is a perspective view of an optical unit of the embodiment showing from the underside thereof.

An optical unit 5 has a box-type housing 30 which is opened upward. In the housing 30, a laser light source, a polygonal mirror, a toroidal lens, a Half-mirror, a spherical mirror, a mirror, a reflector etc. are arranged. An exposure slit 31 is formed at the bottom of the housing 30.

An eraser 32 is arranged at the bottom of the housing 30. The eraser 32 is so constructed that lamps, light emitting diodes, 35 are arranged at plural base portions 34 arranged at a bed plate 33, and is fixed through a base plate 36 to the bottom surface of the housing 30 with attaching portions 37 thereof.

The optical unit 5 having the above construction is fixed to the upper unit 21 with plural bolts 38.

C. IMAGE-FORMING UNIT (IMAGING UNIT) 40

An image-forming unit 40 is so constructed that a photosensitive drum 3, a charger 4, a developing device 7, and a cleaning device 10 are integrally arranged at a unit body 41.

(i) unit body 41 (referring to FIGS. 4-7)

The unit body 41 is constructed by an upper frame 42 and side frames 43 elongated downward from both the sides of the upper frame 42. At the upper frame 42, a charger-attaching portion 44, an exposure slit 45, and eraser insert holes 47 are provided. The exposure slit 45 is able to be opened and closed by a cover 46. At the outer surfaces of the side frames 43, guides 48 and recesses 50 (one of the recesses 50 is not shown) are formed confronting with each other respectively. Each recess 50 has holes 51 and 52 connecting between the inside and the outside thereof.

(ii) Charger 4 (referring to FIGS. 8-12)

The charger 4 has a small holder 61 and a big holder 62, which are made of insulating material, at both the ends of a stabilizer 60 having generally U-like cross-section. The big holder 62 is elongated in a direction perpendicularly intersecting to the longitudinal direction of the stabilizer 60. In the big holder 62, two conductive flat springs 63 and 64 are arranged in the direction perpendicularly intersecting to the longitudinal direction of the stabilizer 60. The one ends of the springs 63 and 64 are supported by support portions 62a and 62b of the big holder 62 which are on the opposite end to the stabilizer 60. The free ends of the springs 63 and 64 are located at a confronting position 62c confronting with the stabilizer 60. Contacts 65 and 66 are arranged at the fixed ends of the springs 63 and 64 to protrude therefrom at the left side of the big holder 62 in FIG. 8.

Figures 8, 9:
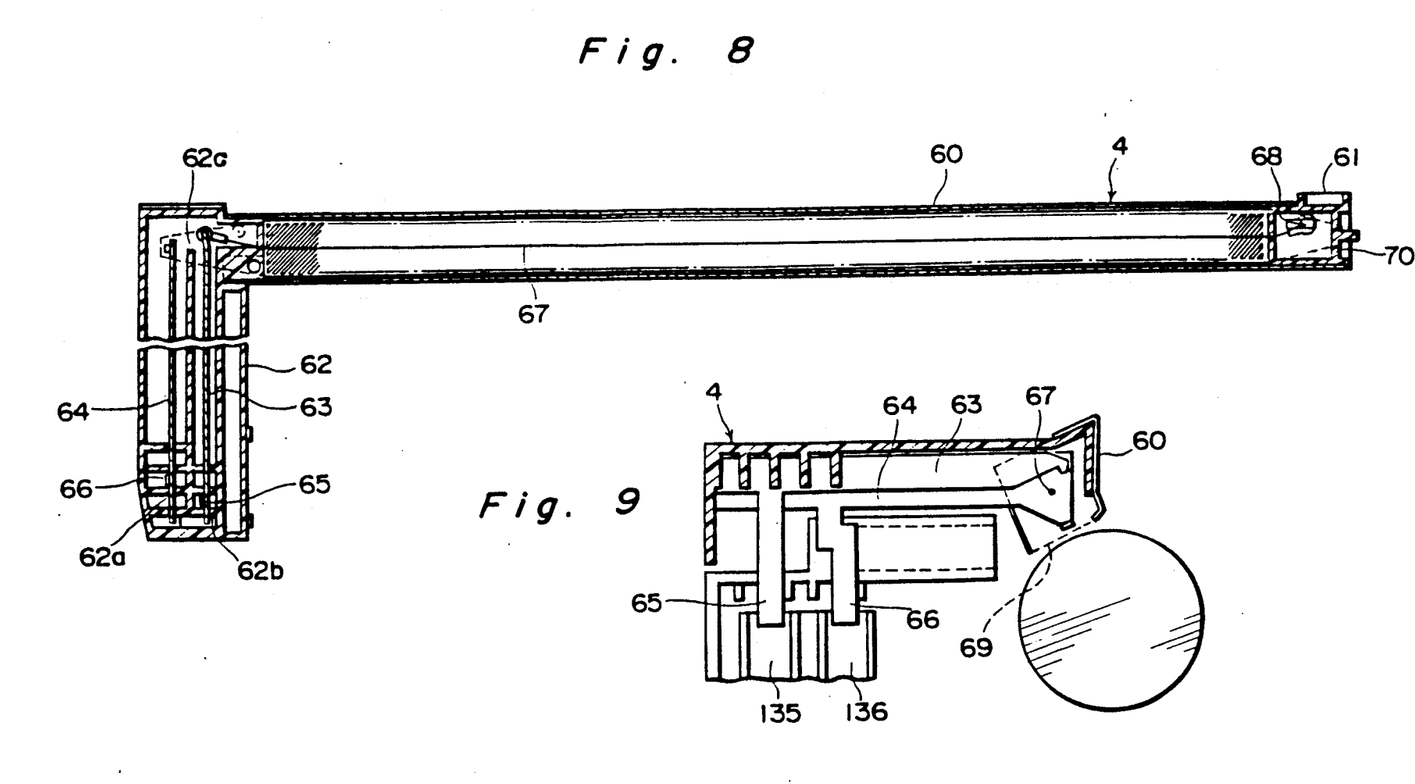
FIG. 8 is a transverse sectional view of a charger of the embodiment.
FIG. 9 is a longitudinal sectional view of the charger.
Figure 10:
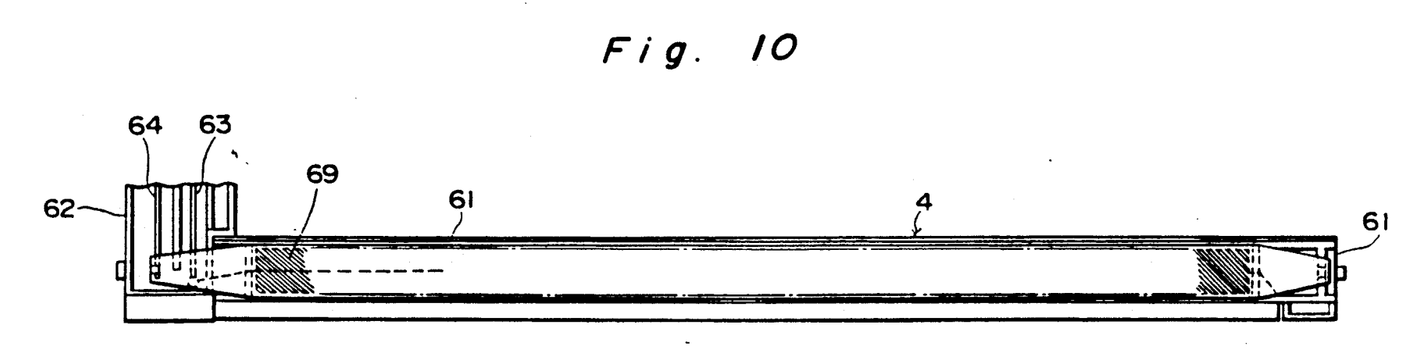
FIG. 10 is a partial bottom view of the charger.
Figure 11:
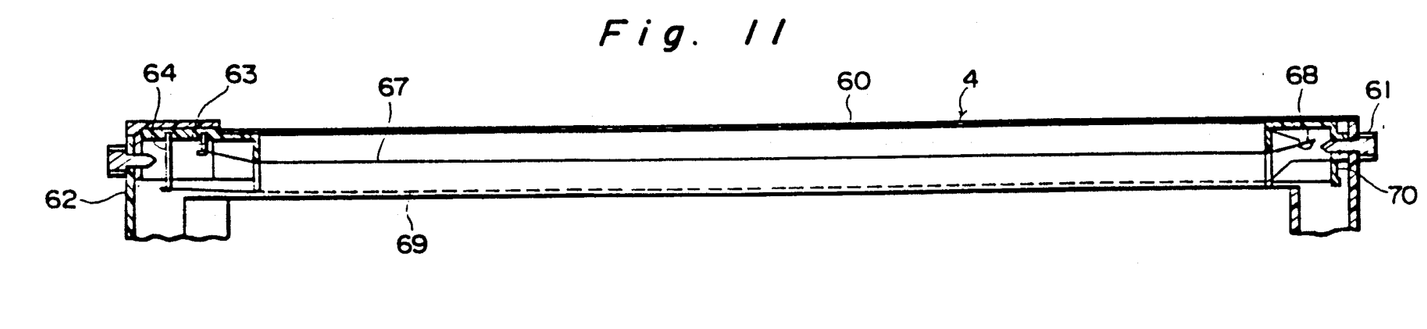
FIG. 11 is a transverse sectional view of the charger.
Figure 12:
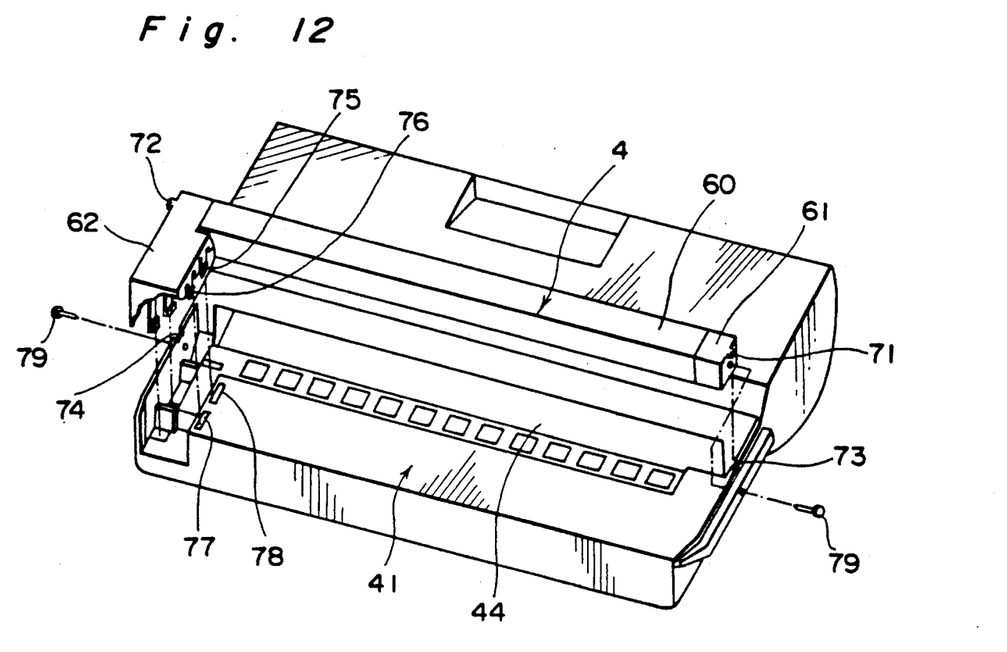
FIG. 12 is a perspective view of the charger attaching to the image-forming unit.

A charge wire 67 is arranged at approximately the middle of the stabilizer 60. The one end of the wire 67 is engaged with a projection 68 of the small holder 61 and the other end thereof is engaged with the free end of the spring 63, so that the wire 67 is tensioned by the restoring force of the spring 63.

A mesh 69 is arranged at the opening of the stabilizer 60. The one end of the mesh 69 is engaged with a projection 70 of the small holder 61 and the other end thereof is engaged with the free end of the spring 64, so that the mesh 69 is tensioned by the restoring force of the spring 64.

The charger 4 having the above-described construction is positioned in a manner described hereinbelow. The stabilizer 60, the small holder 61, and the big holder 62 are fitted into the charger attaching portion 44 of the unit body 41; projections 71 and 72 respectively arranged at the small holder 61 and the big holder 62 are fitted into recesses 73 and 74 of the unit body 41 to prevent the charger 4 from rotating; and positioning pins 79 are respectively inserted into the unit body 41 and the small holder 61 and into the unit body 41 and the big holder 62. In this positioning operation, the charger 4 is fixed to the charger attaching portion 44 by the pins 79 so that the charger 4 is permitted to move in the longitudinal direction thereof. Therefore, this permitted movement can prevent that any overload is forcedly applied to the charger 4 and the unit body 41 by heat deformation thereof. Engaging portions 75 and 76 arranged at the big holder 62 are fitted into engaging holes 77 and 78 of the unit body 41 to prevent them from dropping.

(iii) Developing device 7 (referring to FIGS. 4-7)

The developing device 7 is constructed by a developing unit 80 and a hopper unit 95.

A housing 81 of the developing unit 80 is generally formed in an approximately square, and a driving roller 82, serving as a developing roller, is arranged along the opening of a front portion 81a of the housing 81.

The roller 82 is constructed so that a sleeve 84 made of rubber etc. is covered a mandrel 83, and a gear 86 is attached to the one end of the roller 82. Both the ends of a support shaft 85 of the roller 82 are inserted into grooves 81c formed at both the side walls of the housing 81 to support the roller 82 by bearings 87 fitted into the grooves 81c.

Figure 4:
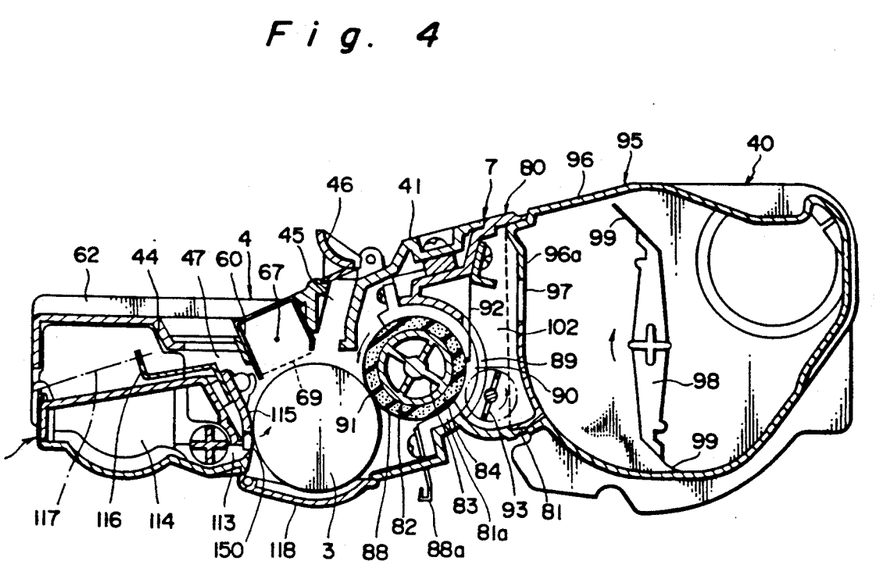
FIG. 4 is a sectional view of an image-forming unit of the embodiment.
Figure 5:
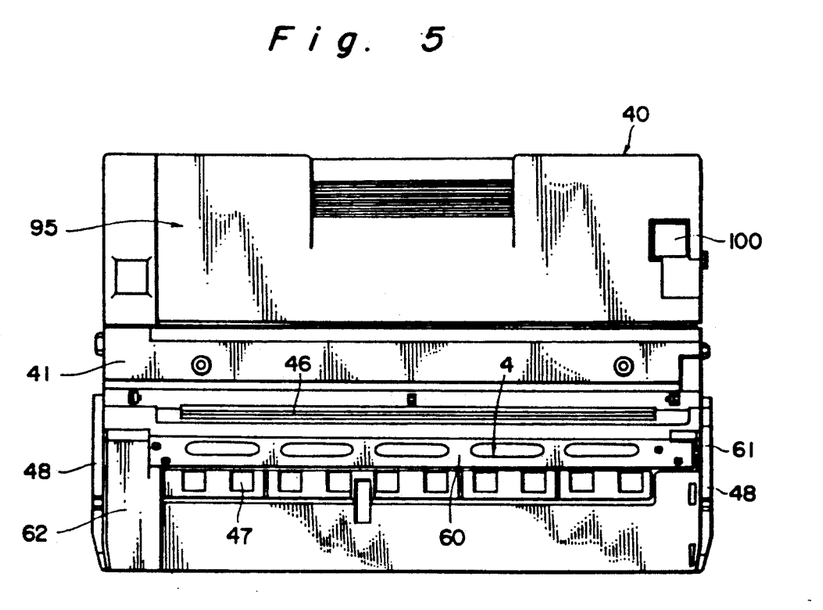
FIG. 5 is a plan view of the image-forming unit.

The roller 82 has a thin film member 88 covered the circumferential surface of the sleeve 84. A sheet made of synthetic resin such as polyamide or polyester, a thin film made of metal such as nickel or chrome, or a sheet which is constructed so that the synthetic resin sheet is laminated over the outer surface of the metal thin film can be used as the thin film member 88. At least a part of the surface of the member 88 is roughened and the circumferential length of the member 88 is a little longer than that of the sleeve 84.

A wall 89 confronting with and spaced from the circumferential surface of both the ends of the roller 82 at specific intervals is formed on the inside of the housing 81. An elastic member 90 is arranged between the wall 89 and the thin film member 88. The thin film member 88 is closely contacted with the circumferential surface of the rear of the driving roller 82. At the front of the driving roller 82, a space 91 is formed between the roller 82 and the member 88. At the bottom of the housing 81, a synthetic resin sheet (not shown) is attached and the free-end-said thereof is contacted with the member 88 under pressure. A contact 88a is arranged at the one end of the housing 81 and the one end thereof contacts with the member 88. A regulating plate 92 is attached to the ceiling of the housing 81 and the free end of the plate 92 contacts with the circumferential surface of the rear 81b of the member 88 under pressure. An agitating blade 93 is arranged in parallel with the driving roller 82 at the rear 81b of the housing 81.

Figure 13:
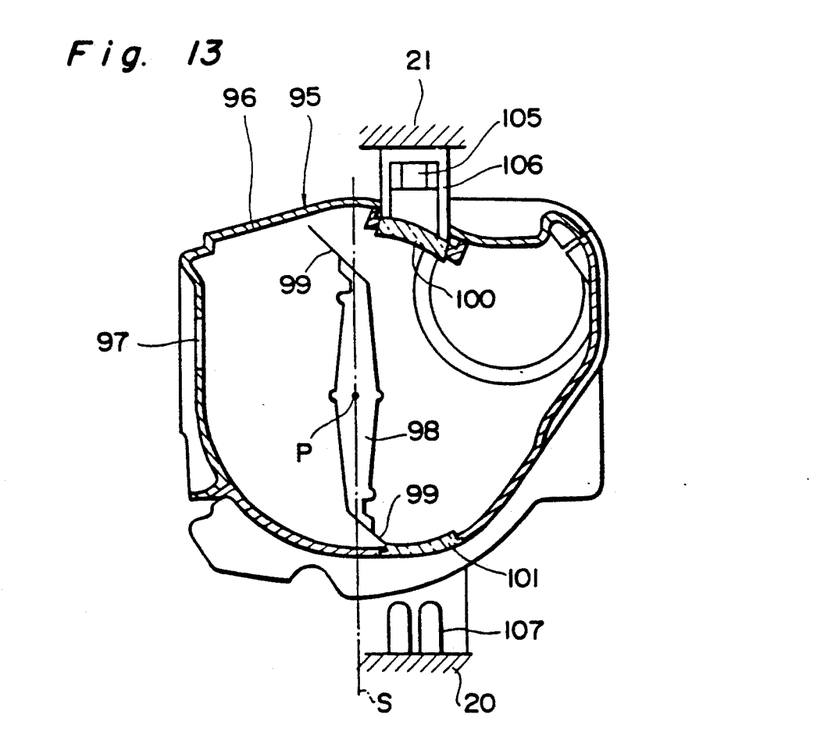
FIG. 13 is a sectional view of a hopper unit of the embodiment.

A hopper 96 of the hopper unit 95 has an opening 97 connecting between the inside and the outside thereof the front 96a of the hopper 96. An agitating blade 98 is rotatably arranged in the hopper 96 and has clean members 99 comprised of a film sheet of polyester etc. at both the distal ends thereof. As shown in FIG. 13, light transmission portions 100 and 101 made of transparent material are arranged at the ceiling and the bottom of the hopper 96 and in the vicinity of a center line (S) in a vertical direction passing a rotary center (P) of the agitating blade 98. The inner surfaces of the portions 100 and 101 are cleaned by the clean members 99 according to rotation of the blade 98. The inner surfaces of the portions 100 and 101 are arranged along the moving locus of the clean members 99 to clean uniformly.

The front of the hopper unit 95 is fitted into the rear of the developing unit 80 and these contact surfaces of them are adhered by adhesive so as to connect the developing unit 80 with the hopper unit 95 to form a unit. The developing unit 80 and the hopper unit 95 are connected with each other to form a buffer space 102 therebetween.

Figure 14:
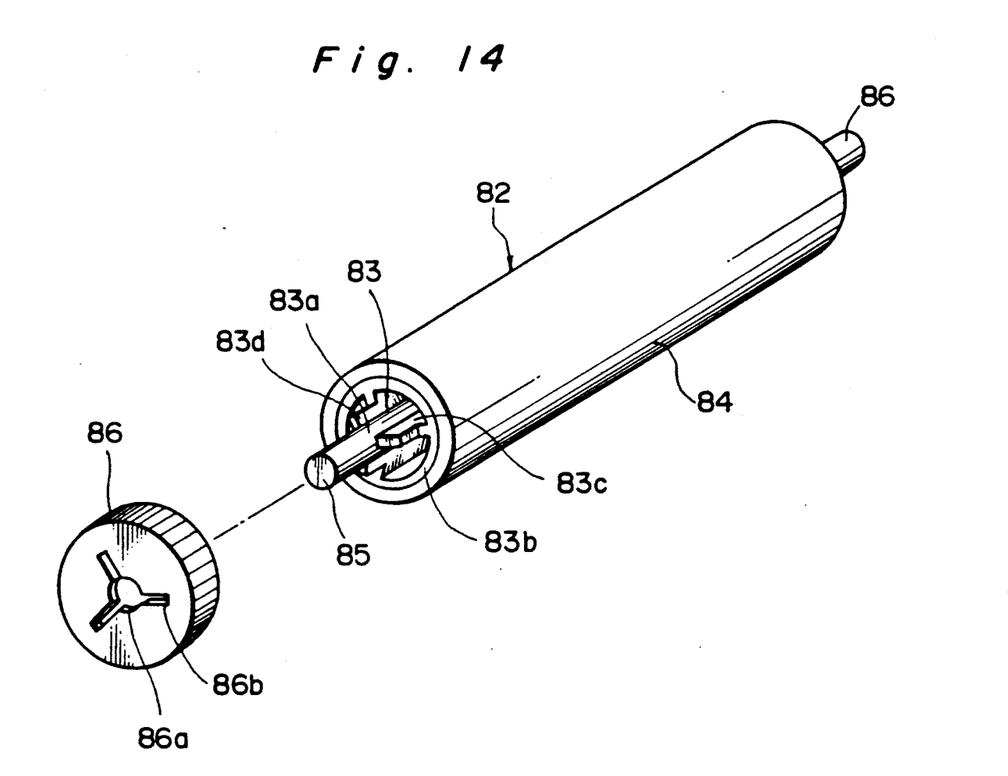
FIG. 14 is an exploded perspective view of a driving roller of the embodiment.

The driving roller 82 will be explained hereinbelow referring to FIG. 14. The mandrel 83 of the driving roller 82 includes a shaft portion 83a, a pipe 83b surrounding the shaft portion 83a, and plural ribs 83c by which the shaft portion 83a is connected with the pipe 83b. The mandrel 83 is formed as a unit by drawing molding or extrusion molding and thereafter the pipe 83b and parts of the ribs 83c in an area predetermined from the end surface of the one end of the mandrel 83 are cut by lathe processing so that the shaft portion 83a and the remainder of the ribs 83c, that is, engaging portions, 83d, are protruded from the pipe 83b. The pipe 83b and all the ribs 83c in an area predetermined from the end surface of the other end thereof are cut so that only the shaft portion 83b is protruded from the pipe 83b. As a result, the shaft portion 83a protruding from the pipe 83b is served as the support shaft 85.

A through hole 86a is formed at the center of the gear 86 and plural slits 86b are radially formed around the hole 86a.

The end of the support shaft 85 of the mandrel 83 of the driving roller 82 is inserted into the hole 86a of the gear 86 and the engaging portions 83d protruded form the pipe 83b are fitted into the slits 86b so that the gear 6 can not relatively rotate with respect to the mandrel 83.

Figure 15:
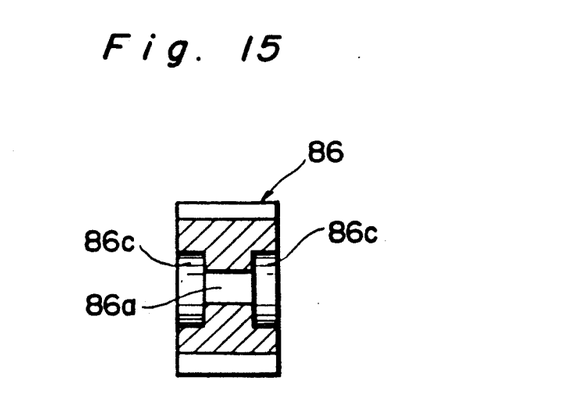
FIG. 15 is a sectional view of a gear of the embodiment.

As shown in FIG. 15, the gear 86 can have slits 86c at both the sides thereof symmetrically. In this case, both the ends of the support shaft 85 can be inserted into the hole 86a of the gear 86, with the result that it is unnecessary to judge both sides of the gear 86 so as to be capable of inserting the support shaft 85 thereinto, particularly in automatic assembly process.

The developing device 7 having the above-described construction is fixed to the unit body 41 by bolts 108 after attaching thereto. The support shaft 85 of the driving roller 82 is held in a state confronting with the hole 51 of the side frame 43.

Figure 6:
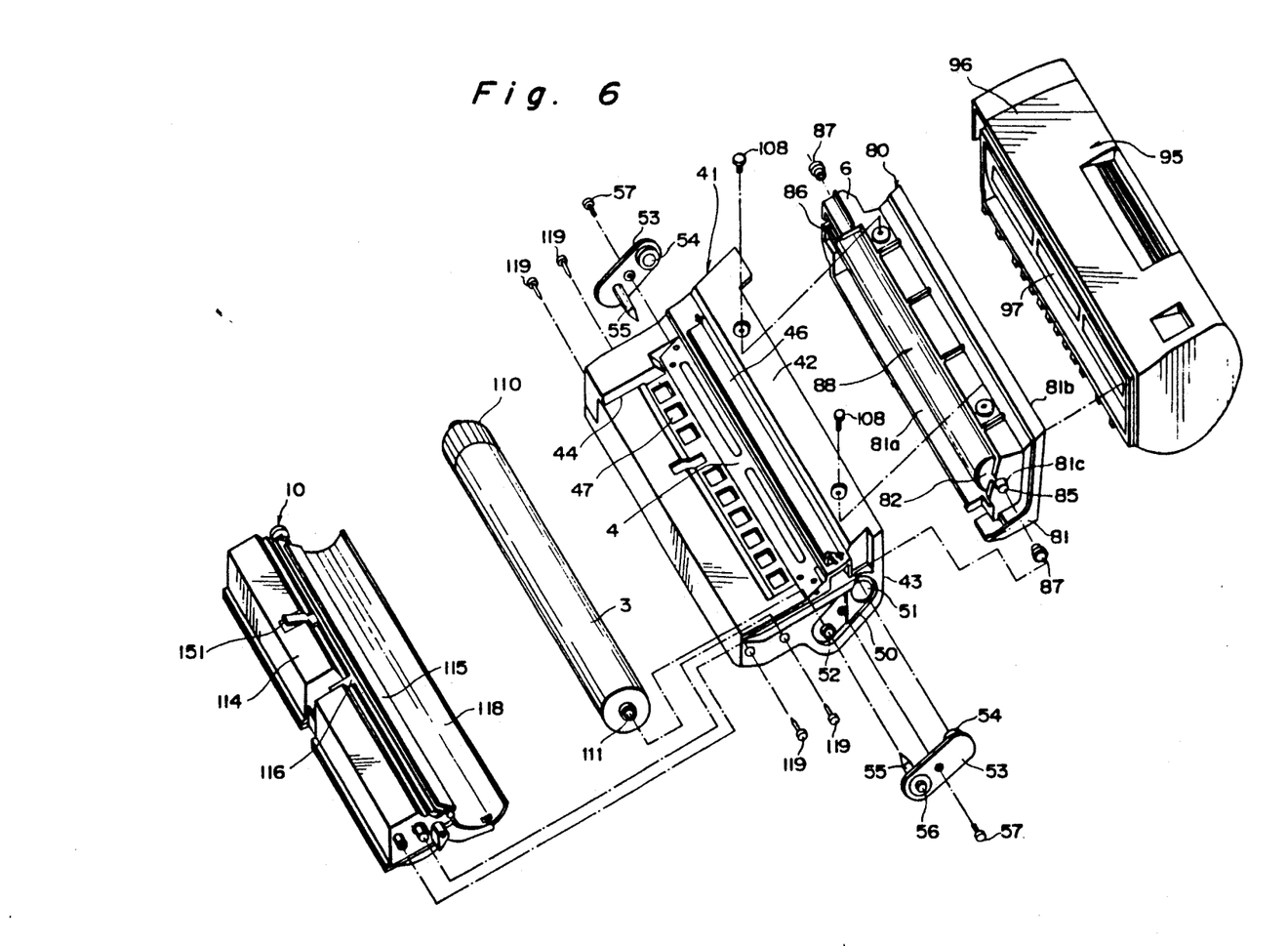
FIG. 6 is an exploded perspective view of the image-forming unit.

(iv) Photosensitive drum 3 (referring to FIG. 6)

The drum 3 is formed so that a photosensitive layer is formed over the circumferential surface of a cylinder element made of material such as aluminum and a gear 110 is attached to the one end of the drum 3.

The drum 3 is arranged inside the unit body 41 while confronting with the driving roller 82 and is fixed to the unit body 41 by holding members 53 for positioning the photosensitive member 3 and the driving roller 82.

Each of the holding members 53 has a plate member with the same shaped as the recess 50 of the side frame 43 of the unit body 41, a support shaft 55 penetrating one end of the plate member, and a bearing 54 arranged at the other end of the plate member. The holding members 53 rotatably support the drum 3 while the bearing 54 and the support shaft 55 are inserted into the holes 51 and 52 respectively and each support shaft 55 is inserted into each bearing hole 111 of the drum 3. At the same time, the bearings 54 are attached on both the ends of the support shaft 85 of the driving roller 82 to support the driving roller 82 rotatably by the holding members 53. The holding members 53 are fitted into and fixed to the recesses 50 by bolts 57.

The drum 3 and the driving roller 82 are respectively supported by the support shafts 55 and the bearings 54 of the holding members 53 having the same shape each other, with the result that the distance between the drum 3 and the roller 82 is maintained constant axially.

Figure 7:
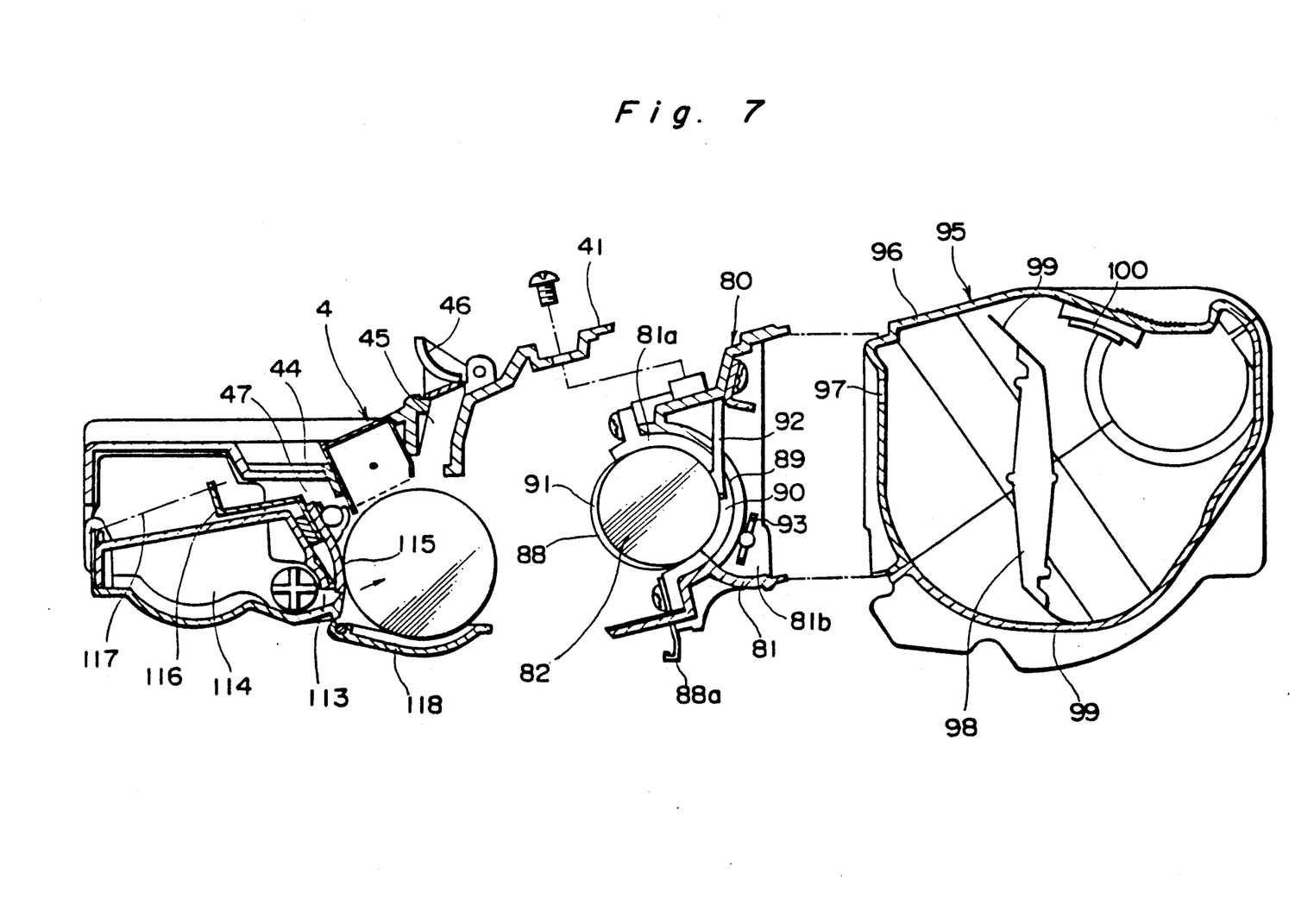
FIG. 7 is an exploded sectional view of the image-forming unit.

(v) Cleaning device 10 (referring to FIGS. 4, 6, and 7)

The cleaning device 10 includes an unnecessary accommodating box 114 having an opening 113 at a position confronting with the drum 3, a cleaner blade 115 arranged near the opening 113, and a seal member 150 consisting of a film element made of material such as urethane. The cleaner blade 115 and an attaching member 116 supporting the cleaner blade 115 are urged by a spring 117 in a direction shown by an arrow in FIGS. 4 and 7. The spring 117 is not set in the urging state when the cleaning device 10 is not used. Once the cleaning device 10 is attached to the unit body 41, a releasing member 151 allows the spring 117 to be set in the urging state in correspondence with the opening operation of the upper unit 21, and thereafter, the urging state is maintained. A cover 118 is attached to the cleaning device 10 to cover the bottom surface of the drum 3.

The cleaning device 10 is attached to the unit body 41 on the opposite side to the developing device 7 through the drum 3 and then is fixed to the side frames 43 of the unit body 41 by positioning pins 119.

D. IMAGE-FORMING UNIT ATTACHING PORTION

As described above, the drum 3, the charger 4, the developing device 7, and the cleaning device 10 are unitedly attached to the unit body 41 to form the image-forming unit 40. The unit 40 is detachably attached to an image-forming unit attaching portion 120 arranged at the upper unit 21 as shown in FIG. 2.

The image-forming unit attaching portion 120 is generally constructed by two frames 121. One of the frames 121 is not shown in the drawings.

Each frame 121 is pivotably supported by each side frame 23 of the upper unit 21 by a shaft 122. Two pins 123 and 124 are arranged at the frame 121. These pins 123 and 124 are respectively inserted into guide grooves 125 and 126 of the side frame 23 formed around the shaft 122 in circular arc to regulate the opening angle of the frame 121. Guides 127 are respectively formed at positions confronting with the frames 121.

The image-forming unit 40 is attached to the upper unit 21 held in the opening state in such a manner that the guides 48 arranged at the side frames 43 of the unit body 41 are inserted between the frames 121 while the guides 48 move along the guides 127. In this attachment, engaging portion (not shown) arranged at one of the frames 121 causes the exposure slit cover 46 of the unit body 41 to rotate to open the exposure slit 45, with the result that the slit 45 is opened and connected with the exposure slit 31 of the optical unit 5 as shown in FIG. 1.

The upper unit 21 to which the image-forming unit 40 has been attached is closed in the direction shown by the arrow (b') in such a manner that the pin 28b is removed from the engaging portions 29a, 29b, and 29c of the guide groove 29 while handling the arm 27 of the open holding mechanism 26.

At this closing operation, according to the closing operation of the upper unit 21, the image-forming unit 40 firstly contacts with the lower unit 20, and then the upper unit 21 is closed over the lower unit 20. Thereafter, the image-forming unit 40 is attached to both the units 20 and 21 in a regular position to move the cover 118 to a position other than a position covering the drum 3, resulting in exposure of the lower surface of the drum 3.

The lamps 35 of the eraser 32 attached to the bottom of the housing of the optical unit 5 are inserted into eraser insert holes 47 of the unit body 41, and the lamps 35 are closely confronted with the drum 3 through a space formed between the charger 4 and the cleaning device 10.

Figure 16:
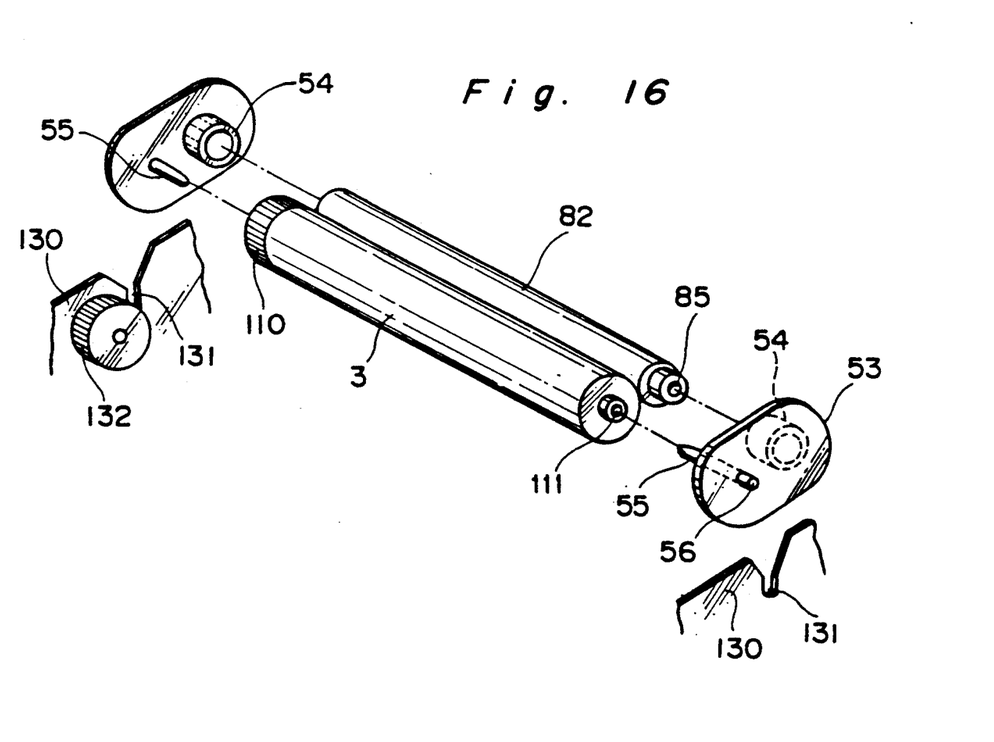
FIG. 16 is an exploded perspective view showing a state where a photosensitive member and the roller are supported by holding members.

As shown in FIG. 16, positioning projections 56 of the support shafts 55 protruding outside the holding members 53 supporting the drum 3 and the driving roller 82 drop into recesses 131 of frames 130 arranged at the lower unit 20, with the result that the holding members 53 are positioned with respect to the frames 130 of the lower unit 20. The gear 110 of the drum 3 brings in engagement with a driving gear 132 arranged at one of the frames 130 to connect the drum 3 with a driving system of the body 2. Similarly, the driving roller 82 and the agitating blades 93 and 98 are connected with the driving system of the body 2.

Thus, the holding members 53 are located on the frames 130 through the projections 56 of the support shafts 55 and the drum 3 is supported by the support shafts 55. Therefore, the drum 3 can be located on the lower unit 20 with good accuracy.

As a result, the gear 110 of the drum 3 can accurately engage with the driving roller 132 to smoothly transfer a driving force from the driving system of the body 2 to the drum 3.

As shown in FIG. 9, the contacts 65 and 66 of the flat springs 63 and 64 arranged at the charger 4 are connected with electric power supply units 135 and 136 of the lower unit 20 to be capable of supplying electric power to the charger 4. Similarly, the contact 88a (referring to FIGS. 4 and 7) arranged at the developing device 7 is connected with an electric power supply unit (not shown) of the body 2.

As shown in FIG. 13, light receiving elements 105 of the upper unit 21 are confronted with the upper light transmission portion 100 of the hopper 95 of the developing device 7. Light emitting elements 107 of the lower unit 20 are confronted with the lower light transmission portion 101. The light receiving elements 105 arranged upward are supported by an elastic light intercepting member 106 to prevent light from entering between the light receiving elements 105 and the light transmission portion 100.

OPERATION

The operation of the printer 1 having the above-described construction will be explained hereinbelow referring to FIG. 1.

In the printer 1, the drum 3 rotates in a direction shown by an arrow (a) to be charged a specified electric potential by the charger 4. A laser beam 6 is illuminated from the optical unit 5 to the charged circumferential surface of the drum 3 charged to form an electrostatic latent image thereon according to information to be reproduced.

Sequentially, the electrostatic latent image is developed into a visible image as a toner image by the developing device 7. The toner image is transferred on a copy paper transporting from a copy paper supply unit 8 to a position confronting with a transfer charger 9.

The paper transferred the toner image is transported to a fixing device 12, and then the toner image is fixed to the paper by heat before the paper to which the toner image has been fixed is discharged to a copy paper discharge unit 13. The toner not transferred on the paper and left on the drum 3 is collected by the cleaning device 10. The electric charge left on the drum 3 is erased by light illumination of the lamps 35 of the eraser 32.

DEVELOPING OPERATION

The operation of the developing device 7 will be explained hereinbelow referring to FIG. 4.

The toner in the buffer space 102 is forcedly transported toward the driving roller 82 by clockwise rotation of the agitating blade 93.

In the other hand, the driving roller 82 rotates counterclockwise and the thin film member 88 rotates counterclockwise with the driving roller 82 by frictional contact between the thin film member 88 and the driving roller 82. The toner in the buffer space 102 adheres to the surface of the thin film member 88 by contact and static electricity force between the thin film member 88 and the toner. The toner adhered is transported with the thin film member 88 counterclockwise. Then, the toner is unitedly coated to form a thin film on the member 88 by the contact portion of the regulating plate 92 and is positively or negatively charged with the friction therebetween.

The toner passed an area contacting with the contact portion of the regulating plate 92 under pressure is moved with the thin film member 88 to transport to a position confronting with the drum 3. Then, according to electric field based on the electric potential difference between the surface potential of the drum 3 and a bias voltage applied on the thin film member 88 through the contact 88a, the toner is moved on the electrostatic latent image formed on the surface of the drum 3 to form the toner image.

Here, the thin film member 88 contacting with the drum 3 has the space 91 between the driving roller 82 and the thin film member 88 and thus the thin film member 88 is not contacted with the driving roller 82. Therefore, the member 88 softly and unitedly contacts with the drum 3 by only its rigidity at a suitable nip width thereof while spacing at specified intervals between the member 88 and the roller 82, with the result that the toner allows the electrostatic latent image on the surface of the drum 3 to unitedly form the toner image.

The toner left on the thin film member 88 without moving to the drum 3 is sequentially transported with the thin film member 88 and fresh toner is supplied to the member 88, having the left toner, at the buffer space 102 again to repeat the above-described operation.

According to the above-described construction, when the toner in the buffer space 102 is consumed, the corresponding amount of fresh toner to the amount of the consumed toner is replenished from the hopper 96 through the opening 97 to the buffer space 102 on the basis of clockwise rotation of the agitating blade 98.

On the other hand, as shown in FIG. 13, at areas above and under the hopper 96, light is emitted from the plural light emitting elements 107 arranged at the lower unit 20 into the hopper 96 through the light transmission portion 101 and then the light emitted into the hopper 96 is detected by the light receiving elements 105 arranged at the upper unit 21 through the light transmission portion 100.

In the hopper 96, the rotation of the agitating blade 98 causes the cleaning members 99 to rotate to simultaneously clean the inner surfaces of the upper and lower light transmission portions 100 and 101 so as to scrap off the toner adhered to the inner surfaces thereof.

Therefore, when the amount of the toner in the hopper 96 is reduced and then the hopper 96 is approximately empty, the cleaning members 99 scrap off the toner adhered on the surfaces of the light transmission portions 100 and 101 before light emitted from the light emitting elements 107 is detected in a given time period by the light receiving elements 105 through the portions 100 and 101 cleaned by the cleaning members 99. The time of period for detecting is longer in correspondence with reduction of the toner. A control device (not shown) samples output signals of the light receiving elements 105. When it is judged in a given time period by the control device that a state where light is detected by the light receiving elements 105 continues, an empty lamp (not shown) arranged at the body 2 is turned on to inform an user of a toner empty state.

A memory with respect to the toner empty state is reset when the upper unit 21 is opened, and after the upper unit 21 is closed, a specified time of period elapses before the sampling operation starts.

Since the plural light emitting elements 107 are arranged, even if there are errors in attaching position and angle of the image-forming unit 40, light emitted from the light emitting elements 107 is certainly detected by the light receiving elements 105.

The outer surface of the upper light transmission portion 100 is located slightly inside the outer surface of the hopper 96 to be capable of preventing any damage in attaching the portion 100 to the upper unit 21 and uneven clean. The outer surface of the lower light transmission portion 101 is located at approximately the same surface as the bottom surface of the hopper 96 and the inner surface of the portion 101 slightly protrudes inside the inner surface of the hopper 96 to be capable of certainly contacting with the cleaning members 99 under pressure for even clean and detecting the toner empty state with good accuracy. These light transmission portions 100 and 101 are arranged while approximately equally spaced from the rotary center (P) of the agitating member 98 and are evenly cleaned by the cleaning members 99.

The light transmission portions 100 and 101 can have lens-shape to collect the light emitted from the light emitting elements 107 so as to illuminate the light receiving elements 105.

In a case where a copy paper passes just under the hopper 95, the light emitting elements 107, the light receiving elements 105, and the light transmission portions 100 and 101 are preferably arranged outside a passage of the paper.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An image-forming apparatus comprising:
   an image-forming unit detachably attached to a body of the apparatus and having a photosensitive member rotatably on a first rotary axis and a roller member rotatably on a second rotary axis;
   a holding member arranged to said image-forming unit and having a first holding portion for holding the first rotary axis, a second holding portion for holding the second rotary axis and a positioning member so shaped to be protuberant, whereby the photosensitive member and the roller member being held at specific intervals in said image-forming unit; and
   an engaging member provided at the body and having a notch portion, said engaging member engaging with the protuberance of the holding member at the notch portion when said image-forming unit is attached to the body, whereby said image-forming unit is positioned to the body.

2. An image-forming apparatus as claimed in claim 1, wherein said image-forming unit has a recess for fitting said holding member therein, the first and second holding portions of said holding member are arranged at a side of said holding member which side is fitted into the recess, and the positioning member is arranged at the opposite side.

3. An image-forming apparatus as claimed in claim 2, wherein a first driving force transferring unit for transferring a driving force for driving the photosensitive member is arranged at the body of the apparatus, a second driving force transferring unit for engaging with the first driving force transferring unit to transfer the driving force to the photosensitive member, and the first and second driving force transferring units being positioned by the positioning member when said image-forming unit is attached to the body.

4. An image-forming apparatus as claimed in claim 1, wherein said roller member is a developing roller for supplying developer on an outer surface of the photosensitive member.

5. An image-forming apparatus as claimed in claim 4, wherein said image-forming apparatus further comprises a cleaning device for removing the developer left on the photosensitive member therefrom.

6. An image-forming apparatus having an image-forming unit detachably attached to a body of the apparatus, the image-forming unit integrally holding, at least, a photosensitive member and a developing roller, the apparatus comprising:
   a first frame having a holding means for detachably holding the image-forming unit, and an exposure means for forming an electrostatic latent image on an outer surface of the photosensitive member in the image-forming unit by exposure;
   a second frame holding said first frame to be capable of opening and closing it with respect thereto, and having a copy paper transporting means, a transfer means for transferring the image on the photosensitive member onto the paper, and a driving force transferring means for transferring a driving force to the image-forming unit;
   a holding member attached to the image-forming unit, having a first holding portion for holding a rotary shaft of the photosensitive member, a second holding portion for holding a rotary shaft of the developing roller and a positioning member, whereby said holding member holding the photosensitive member and the developing roller are spaced at specific intervals in the image-forming unit; and
   an engaging member provided at said second frame, and moving into engagement with the positioning member when said first frame holding the image-forming unit is closed with respect to said second frame, whereby the image-forming unit is positioned at a specified position with respect to said second frame.

7. An image-forming apparatus as claimed in claim 6, wherein said second frame has a first driving force transferring means for transferring a driving force to the image-forming unit, the image-forming unit has a second driving force transferring means for engaging with the first driving force transferring means to receive the force therefrom when said first frame is closed with respect to said second frame, and said engaging member brings into engagement with the positioning member when said first frame holding the image-forming unit is closed with respect to said second unit, whereby the first and second driving force transferring means are positioned in a predetermined positioning relation.

8. An image-forming apparatus as claimed in claim 6, wherein the exposure means allows a laser beam to illuminate the outer surface of the photosensitive member.

9. An image-forming apparatus comprising:
   an image-forming unit detachably attached to a body of the apparatus and having a photosensitive member rotatable in a first rotary axis, and a roller member rotatable in a second rotary axis;
   a holding member attached to said image-forming unit and having a first portion for holding the first rotary axis, a second portion for holding the second rotary axis, and a third portion extended from the first rotary axis for positioning said image-forming unit at a specified position in the body so as to hold the photosensitive member and the roller member at predetermined intervals in said image-forming unit; and
   an engaging member attached to the body thereof for engagement with the third portion of the holding member when said image-forming unit is attached to the body, whereby said image-forming unit is positioned to the body.

10. An image-forming apparatus as claimed in claim 9, wherein said holding member has a first holding member for holding the first rotary axis at the first portion, a second holding member for holding the second rotary axis at the second portion, a pin extended from the first rotary axis and a plate for integrally supporting the first and second holding members and the pin.

11. An image-forming apparatus comprising:
    an image-forming unit detachably attached to a body of the apparatus and having a photosensitive member rotatable on a first rotary axis, and a roller member rotatable on a second rotary axis;
    a holding member attached to said image-forming unit and having a first portion for holding the first rotary axis and a second portion for holding the second rotary axis so as to hold the photosensitive member and the roller member at predetermined intervals in said image-forming unit, said holding means further having a third portion coaxial with the first rotary axis for positioning said image-forming unit at a specified position in the body; and an engaging member provided at the body thereof for engagement with the third portion of the holding member when said image-forming unit is attached to the body, whereby said photosensitive member in the image-forming unit is accurately positioned to the body.

12. An image-forming apparatus as claimed in claim 11, wherein said third portion of the holding member is so shaped to be a protuberance coaxial with the first rotary axis.

13. An image-forming apparatus having an image-forming unit detachably attached to a body of the apparatus, the image-forming unit integrally holding, at least, a photosensitive member and a developing roller, the apparatus comprising:
a first frame having a holding member for detachably holding the image-forming unit;
a second frame holding said first frame to be capable of opening and closing it with respect thereto;
a holding member attached to the image-forming unit and having a first portion for holding the first rotary axis and a second portion for holding the second rotary axis so that the photosensitive member and the developing roller are spaced at specific intervals in the image-forming unit, said holding means further having a third portion coaxial with the first rotary axis for positioning said image-forming unit at a specified position in the apparatus body; and
an engaging member provided at the second frame for engaging with the third portion of the holding member when the first frame holding the image-forming unit is closed with respect to the second frame, whereby the photosensitive member in the image-forming unit is accurately positioned at a specified position with respect to the second frame.

14. An image-forming apparatus as claimed in claim 13, wherein said third portion of the holding member is so shaped to be a protuberance coaxial with the first rotary axis.

15. An image-forming apparatus comprising:
a first frame and a second frame pivotally movable with respect to the first frame;
an image-forming unit having a photosensitive member rotatably on a first rotary axis and a roller member rotatably on a second rotary axis;
a third frame provided between the first and second frames for detachably holding the image-forming unit;
a holding member arranged to said image-forming unit having a first holding portion for holding the first rotary axis, a second holding portion for holding the second rotary axis and a positioning member so shaped to be protuberant, whereby the photosensitive member and the roller member being held at specific intervals in said image-forming unit; and
an engaging member provided at the first frame and having a notch portion, said engaging member engaging with the protuberance of the holding member at the notch portion when the second frame is closed with respect to the first frame through the third frame holding the image-forming unit, whereby said image-forming unit is positioned to the first frame.

16. In an image-forming apparatus having a first frame and a second frame holding said first frame to be capable of opening and closing it with respect thereto, a method comprising the steps of:
providing a holding member to the image-forming unit;
holding a photosensitive member and developing roller in the image-forming unit at specific intervals by the holding member;
providing a positioning member to the image forming apparatus body;
attaching the image-forming unit to the first frame; and
engaging the holding member with the positioning member when the first frame to which the image-forming unit is attached is closed with respect to the second frame.

17. An image-forming apparatus comprising:
an image-forming unit detachably attached to a body of the apparatus and having a latent image bearing member rotatably on a first rotary axis, and a roller member rotatable on a second rotary axis;
a holding member attached to said image-forming unit and having a first portion for holding the first rotary axis, a second portion for holding the second rotary axis and a third portion extended from the first rotary axis for positioning said image-forming unit at a specified position in the body so as to hold the latent image bearing member and the roller member at predetermined intervals in said image-forming unit; and
an engaging member attached to the body thereof for engagement with the third portion of the holding member when said image-forming unit is attached to the body, whereby said image-forming unit is positioned to the body.

18. An image-forming apparatus as claimed in claim 17, wherein said holding member has a first holding member for holding the first rotary axis at the first portion, a second holding member for holding the second rotary axis at the second portion, a pin extended from the first rotary axis and a plate for integrally supporting the first and second holding members and the pin.

19. An image-forming apparatus comprising:
an image-forming unit detachably attached to a body of the apparatus and having a latent image bearing member rotatable on a first rotary axis and a roller member rotatable on a second rotary axis;
a holding member arranged to said image-forming unit and having a first holding portion for holding the first rotary axis, a second holding portion for holding the second rotary axis and a positioning member so shaped to be protuberance, whereby the latent image bearing member and the roller member are held at specific intervals in said image-forming unit; and
an engaging member provided at the body and having a notch portion, said engaging member engaging with the protuberance of the holding member at the notch portion when said image-forming unit is attached to the body, whereby said image-forming unit is positioned to the body.

20. An image-forming apparatus as claimed in claim 19, wherein said image-forming unit has a recess for fitting said holding member therein, the first and second holding portions of said holding member are arranged at a side of said holding member which side is fitted into the recess, and the positioning member is arranged at an opposite side.

21. An image-forming apparatus as claimed in claim 19, wherein a first driving force transferring unit for transferring a driving force for driving the latent image bearing member is arranged at the body of the apparatus, a second driving force transferring unit is engaged with the first driving force transferring unit to transfer the driving force to the latent image bearing member, and the first and second driving force transferring units are positioned by the positioning member when said image-forming unit is attached to the body.

22. An image-forming apparatus comprising:
an image-forming unit detachably attached to a body of the apparatus and having a latent image bearing member rotatable on a first rotary axis, and a roller member rotatable on a second rotary axis;
a holding member attached to said image-forming unit and having a first portion for holding the first rotary axis and a second portion for holding the second rotary axis so as to hold the latent image bearing member and the roller member at predetermined intervals in said image-forming unit, said holding member further having a third portion coaxial with the first rotary axis for positioning said image-forming unit at a specified position in the body; and
an engaging member provided at the body thereof for engagement with the third portion of the holding member when said image-forming unit is attached to the body, whereby the latent image bearing member in the image-forming unit is accurately positioned to the body.

23. An image-forming apparatus as claimed in claim 22, wherein said third portion of the holding member is so shaped to be a protuberance coaxial with the first rotary axis.

24. An image-forming apparatus comprising:
a first frame;
a second frame pivotably movable with respect to the first frame;
an image-forming unit having a latent image bearing member rotatable on a first rotary axis and a roller member rotatable on a second rotary axis;
a third frame provided between the first and second frames for detachably holding the image-forming unit;
a holding member arranged on said image-forming unit and having a first holding portion for holding the first rotary axis, a second holding portion for holding the second rotary axis and a positioning member so shaped to be protuberant, whereby the latent image bearing member and the roller member being held at specific intervals in said image-forming unit; and
an engaging member provided at the first frame and having a notch portion, said engaging member engaging with the protuberance of the holding member at the notch portion when the second frame is closed with respect to the first frame through the third frame holding the image-forming unit, whereby said image-forming unit is positioned to the first frame.

25. An image forming unit for attachment to an image-forming apparatus and supporting a latent image bearing member rotatably around a first rotary axis and a roller member rotatably around a second rotary axis therein, said image-forming unit comprising:
a pair of holding members for holding the latent image bearing member and the roller member at both sides of the image-forming unit;
a pair of shafts respectively penetrating the holding members, a portion of said shafts being projected from the holding member toward an inner side of the unit for holding the latent image bearing member to be rotatable around the first rotary axis, and another portion of the shaft being projected from the holding member toward an outside of the unit to be engaged with a notch portion of the image-forming apparatus; and
a holding portion provided at a predetermined distance from the shaft in each of the holding members for holding the roller member to be rotatable around the second rotary axis, whereby the latent image bearing member and the roller member are held at specific intervals in the image-forming unit and the image-forming unit is positioned at a predetermined position of the image-forming apparatus when the image-forming unit is attached to the image-forming apparatus.

26. An image-forming unit for attachment to an image-forming apparatus, said image-forming unit comprising:
a latent image bearing member rotatable around a first rotary axis;
a roller member rotatable around a second rotary axis;
a holding member having a first portion for holding the first rotary axis and a second portion for holding the second rotary axis so as to hold the latent image bearing member and the roller member at predetermined intervals; and
a positioning member included on said holding member and extended from the first rotary axis for positioning the image forming unit at a specified position in the image forming apparatus when the image-forming unit is attached to the image-forming apparatus.

27. An image-forming unit as claimed in claim 26, wherein said positioning member engages with an engaging member on the image forming apparatus.

28. An image-forming unit as claimed in claim 26, wherein said holding member has a first holding member for holding the first rotary axis at the first portion, a second holding member for holding the second rotary axis at the second portion, a pin extended from the first rotary axis and a plate for integrally supporting the first and second holding members and the pin.

29. An image-forming unit for attachment to an image-forming apparatus, said image-forming unit comprising:
a latent image bearing member rotatable around a first rotary axis;
a roller member rotatable around a second rotary axis; and
a holding member having a first portion for holding the first rotary axis and a second portion for holding the second rotary axis so as to hold the latent image bearing member and roller member at predetermined intervals, and further having a third portion coaxial with the first rotary axis for positioning the image forming unit at a specified position in the image forming apparatus when the image-forming unit is attached to the image-forming apparatus.

30. An image-forming unit as claimed in claim 29, wherein said third portion of the holding member engages with an engaging member on the image forming apparatus.

31. An image-forming unit as claimed in claim 30, wherein said positioning member is so shaped to be protuberance coaxial with the first rotary axis and said engaging member has a notch portion engaged with said protuberance.

* * * * *